United States Patent
Dow et al.

(10) Patent No.: US 6,518,431 B2
(45) Date of Patent: Feb. 11, 2003

(54) PROCESS FOR PREPARING SUBSTITUTED PYRIDINES

(75) Inventors: Robert L. Dow, Waterford, CT (US); Steven R. Schneider, Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/820,137

(22) Filed: Mar. 28, 2001

(65) Prior Publication Data

US 2002/0077478 A1 Jun. 20, 2002

Related U.S. Application Data

(60) Provisional application No. 60/193,772, filed on Mar. 31, 2000.

(51) Int. Cl.[7] .................. C07D 401/02; C07D 213/02
(52) U.S. Cl. .................. 546/282.1; 546/283.1; 546/339
(58) Field of Search .................. 546/282.1, 283.1, 546/339

(56) References Cited

U.S. PATENT DOCUMENTS

| 5,561,142 A | 10/1996 | Fisher et al. ............ 546/335 |
| 5,792,871 A | 8/1998 | Chartrain et al. ......... 546/312 |

FOREIGN PATENT DOCUMENTS

| WO | WO9832753 | 7/1998 |
| WO | WO0048997 | 8/2000 |

OTHER PUBLICATIONS

J.Y.L. Chung, et al., *Practical chemoenzymatic synthesis of a 3–pyrodylethanolamino $\beta_3$ adrenergic receptor agonist*, Tetrahedron Letters, vol. 40, 1999, pp. 6739–6743.

E.R. Parmee, et al., *Human $\beta_3$ Adrenergic Receptor Agonists Containing Cyclic Ureidobenzenesulfonamides*, Bioorganic & Medical Chemistry Letters, vol. 9, 1999, pp. 749–754.

E.M. Naylor, et al., *Human $\beta_3$ Adrenergic Receptor Agonists Containing Imidazolidinone and Imidazolone Benzenesulfonamides*, Bioorganic & Medicinal Chemistry Letters, vol. 9, 1999, pp. 755–758.

T.L. Shih et al., *L–770,644: A Potent and Selective Human $\beta_3$ Adrenergic Receptor Agonist with Improved Oral Bioavailability*, Bioorganic & Medicinal Chemistry Letters, vol. 9, 1999, pp. 1251–1254.

Primary Examiner—Zinna Northington Davis
(74) Attorney, Agent, or Firm—Peter C. Richardson; Gregg C. Benson; Martha A. Gammill

(57) ABSTRACT

A process for preparing a compound of the formula

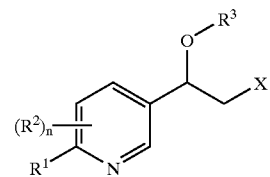

IX wherein n, $R^1$, $R^2$, $R^3$ and X are as defined above, used as an intermediate in the synthesis of β-adrenergic receptor agonists.

17 Claims, No Drawings

PROCESS FOR PREPARING SUBSTITUTED PYRIDINES

CROSS REFERENCE TO RELATED APPLICATION

This non-provisional application is based upon and claims priority from U.S. provisional application No. 60/193,772, filed Mar. 31, 2000.

BACKGROUND OF THE INVENTION

The present invention relates to a process for preparing substituted pyridines which are intermediates in the synthesis of β-adrenergic receptor agonists useful as hypoglycemic and antiobesity agents, increasing lean meat deposition and/or improving the lean meat to fat ratio in edible animals. The β-adrenergic receptor agonists further possess utility in the treatment of intestinal motility disease disorders, depression, prostate disease, dyslipidemia and airway inflammatory disorders such as asthma and obstructive lung disease.

The disease diabetes mellitus is characterized by metabolic defects in production and/or utilization of carbohydrates which result in the failure to maintain appropriate blood sugar levels. The result of these defects is elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type I diabetes, or insulin-dependent diabetes, is the result of an absolute deficiency of insulin, the hormone which regulates carbohydrate utilization. Type II diabetes, or non-insulin dependent diabetes, often occurs with normal, or even elevated levels of insulin and appears to be the result of the inability of tissues to respond appropriately to insulin. Most of the Type II diabetics are also obese.

The β-adrenergic receptor agonists effectively lower blood glucose levels when administered orally to mammals with hyperglycemia or diabetes.

The β-adrenergic receptor agonists also reduce body weight or decrease weight gain when administered to mammals. The ability of β-adrenergic receptor agonists to affect weight gain is due to activation of β-adrenergic receptors which stimulate the metabolism of adipose tissue.

β-Adrenergic receptors have been categorized into $β_1$-, $β_2$- and $β_3$-subtypes. Agonists of β-receptors promote the activation of adenyl cyclase. Activation of $β_1$-receptors invokes increases in heart rate while activation of $β_2$-receptors induces relaxation of skeletal muscle tissue which produces a drop in blood pressure and the onset of smooth muscle tremors. Activation of $β_3$-receptors is known to stimulate lipolysis (the breakdown of adipose tissue triglycerides to glycerol and free fatty acids) and metabolic rate (energy expenditure), and thereby promote the loss of fat mass. Compounds that stimulate β-receptors are, therefore, useful as anti-obesity agents, and can also be used to increase the content of lean meat in edible animals. In addition, compounds which are $β_3$-receptor agonists have hypoglycemic and/or anti-diabetic activity, but the mechanism of this effect is unknown.

Until recently $β_3$-adrenergic receptors were thought to be found predominantly in adipose tissue. $β_3$-Receptors are now known to be located in such diverse tissues as the intestine (*J. Clin. Invest.*, 91, 344 (1993)) and the brain (*Eur. J. Pharm.*, 219,193 (1992)). Stimulation of $β_3$-receptors have been demonstrated to cause relaxation of smooth muscle in colon, trachea and bronchi. *Life Sciences*, 44(19), 1411 (1989); *Br. J. Pharm.*, 112, 55 (1994); *Br. J. Pharmacol*, 110, 1311 (1993). For example, stimulation of $β_3$-receptors has been found to induce relaxation of histamine-contracted guinea pig ileum, *J. Pharm. Exp. Ther.*, 260, 1, 192 (1992).

The $β_3$-receptor is also expressed in human prostate. Because stimulation of $β_3$-receptors cause relaxation of smooth muscles that have been shown to express the $β_3$-receptor (e.g. intestine), one skilled in the art would predict relaxation of prostate smooth muscle. Therefore, $β_3$-agonists will be useful for the treatment or prevention of prostate disease.

SUMMARY OF THE INVENTION

The present invention relates to a process for preparing a compound of the formula

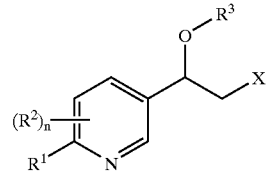

IX wherein n is 0, 1, 2 or 3;

$R^1$ is hydrogen or halo;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ or $NR^4CO_2 R^4$;

$R^3$ is tetrahydrofuranyl, tetrahydropyranyl or a silyl protecting group;

X is halo, methanesulfonyloxy, benzenesulfonyloxy, p-toluenesulfonyloxy, m-nitrobenzenesulfonyloxy or p-nitrobenzenexulfonyloxy;

$R^4$ and $R^5$, for each occurrence, are each independently selected from hydrogen, $(C_1-C_{10})$alkyl, $(C_1-C_{10})$alkoxy, $(C_3-C_8)$cycloalkyl,$(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above;

comprising reacting a compound of the formula

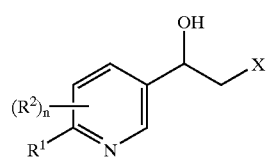

X wherein n, $R^1$, $R^2$ and X are as defined above, with a silyating agent in the presence of a base.

The term "alkyl", as used herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

The term "halo", as used herein, unless otherwise indicated, includes fluoro, chloro, bromo or iodo.

$(C_2–C_9)$Heterocycloalkyl when used herein includes, but is not limited to, pyrrolidinyl, tetrahydrofuranyl, dihydrofuranyl, tetrahydropyranyl, pyranyl, thiopyranyl, aziridinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc.

$(C_2–C_9)$Heteroaryl when used herein includes, but is not limited to, furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, etc.

The term "silyl protecting group", when used herein includes, but is not limited to, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

The present invention further relates to a process wherein the silyating agent is tert-butyldimethylsilyl chloride, triethylchlorosilane, triisopropylchlorosilane or diphenylmethylchlorosilane.

The present invention further relates to a process wherein the base is triethylamine, N,N-diisopropylethylamine, imidazole, pyridine, 2,6-lutidine or N-methylmorpholine.

The present invention further relates to a process wherein the compound of the formula

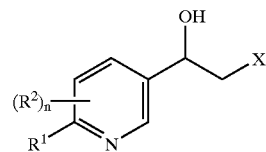

X is formed by reacting a compound of the formula

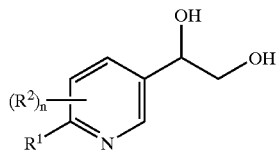

XI wherein n, $R^1$ and $R^2$ are as defined above, with a sulfonyl chloride in the presence of a base, and in the case wherein X is halo, by further treatment with a metal halide.

The present invention further relates to a process wherein the sulfonyl chloride is p-toluenesulfonyl chloride, methanesulfonyl chloride, m-nitrobenzenesulfonyl chloride, p-nitrobenzenesulfonyl chloride or benezenesulfonyl chloride.

The present invention further relates to a process wherein the base is triethylamine, diisopropylethylamine, pyridine, 2,4,6-collidine or 2,6-lutidine.

The present invention further relates to a process wherein the metal halide is lithium chloride.

The present invention further relates to a process wherein the compound of the formula

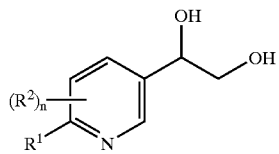

XI is formed by reacting a compound of the formula

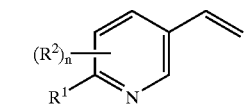

XII wherein n, $R^1$ and $R^2$ are as defined above, with a dihydroxylating agent, with or without a co-oxidant and/or a coordinating ligand.

The present invention further relates to a process wherein the dihydroxylating agent is osmium tetroxide or potassium permanganate.

The present invention further relates to a process wherein the co-oxidant is potassium ferricyanide, hydrogen peroxide, tert-butyl hydroperoxide or N-methylmorpholine-N-oxide.

The present invention further relates to a process wherein the coordinating ligand is hydroquinidine 1,4-phthalazinediyl diether or hydroquinine 1,4-phthalazinediyl diether.

The present invention further relates to a process wherein the compound of the formula

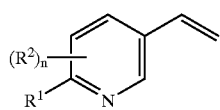

is formed by reacting a compound of formula V

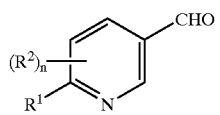

wherein n, $R^1$ and $R^2$ are as defined above, with a methylating reagent.

The present invention further relates to a process wherein the methylating reagant is prepared from methyltriphenylphosphonium bromide and potassium tert-butoxide.

The present invention further relates to a process wherein the compound of the formula

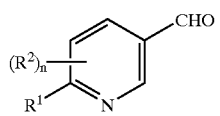

is formed by reducing a compound of the formula

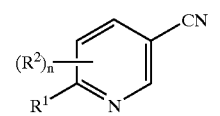

wherein n, $R^1$ and $R^2$ are as defined above, with a reducing agent followed by hydrolysis with an acid or base.

The present invention further relates to a process wherein the reducing agent is diisobutylaluminum hydride.

The present invention further relates to a process wherein the acid is sulfuric acid.

The present invention relates to a process for preparing a compound of the formula

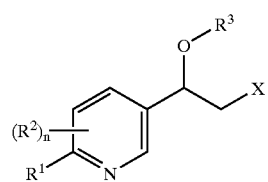

wherein n is 0, 1, 2 or 3;
$R^1$ is hydrogen or halo;
each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ and $NR^4CO_2R^4$;
$R^3$ is tetrahydrofuranyl, tetrahydropyranyl or a silyl protetcting group;
X is halo, methanesulfonyloxy, benzenesulfonyloxy, p-toluenesulfonyloxy, m-nitrobenzenesulfonyloxy or p-nitrobenzenexulfonyloxy;

$R^4$ and $R^5$ are each independently selected from hydrogen, $(C_1-C_{10})$alkyl, $(C_1-C_{10})$alkoxy, $(C_3-C_8)$cycloalkyl, $(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl or $(C_1-C_6)$alkoxy;
or $R^5$ is $N(R^4)_2$ wherein $R^4$ is as defined above; and
comprising
(a) reacting a compound of the formula

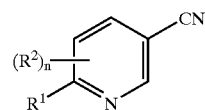

wherein n, $R^1$ and $R^2$ as defined above, with a reducing agent followed by hydrolsis with an acid or base;
(b) reacting the intermediate of formula XIII so formed

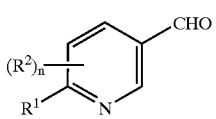

wherein n, $R^1$ and $R^2$ are as defined above, with a methylating agent to form a vinylpyridine compound of the formula

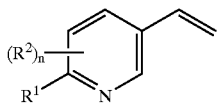

(c) reacting the vinylpyridine compound so formed in step (b) with a dihydroxylating agent, with or without a co-oxidant and/or a coordinating ligand to form a compound of the formula

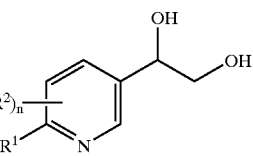

wherein n, $R^1$ and $R^2$ are as defined above;
(d) reacting the compound of formula XI so formed with a sulfonyl chloride in the presence of a base to form a compound of the formula X

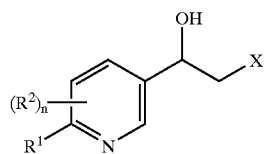

wherein n, $R^1$, $R^2$ and X are as defined above; and (e) reacting the compound of formula X so formed with silyating agent in the presence of a base.

The present invention relates to a process for preparing a compound of the formula

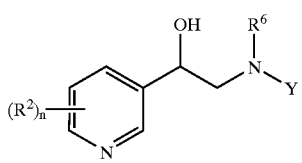

wherein n is 0, 1, 2 or 3;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ or $NR^4CO_2R^4$;

$R^4$ and $R^5$, for each occurrence, are each independently selected from hydrogen, $(C_1-C_{10})$alkyl, $(C_1-C_{10})$alkoxy, $(C_3-C_8)$cycloalkyl, $(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above;

$R^6$ is $COR^7$ or $CO_2R^7$ wherein $R^7$ is $(C_1-C_8)$alkyl; and Y is

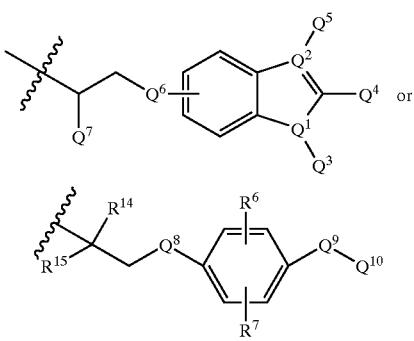

wherein:

$Q^1$ is oxygen, nitrogen or sulfur;

$Q^2$ is carbon or nitrogen;

$Q^3$ is hydrogen, $-(CH_2)_q$-phenyl, $-(C_1-C_{10})$alkyl, $-(CH_2)_q-NG^1G^2$, $-(CH_2)_q-CO_2G^3$, $-(CH_2)_q-CO-NG^1G^2$, $-(CH_2)_q-OG^3$, $-(CH_2)_q-SO_3G^3$, $-(CH_2)_q-SO_2-(C_1-C_6)$alkyl, $-(CH_2)_q-SO_2NG^1G^2$, or a heterocycle selected from the group consisting of $-(CH_2)_q$-pyridyl, $-(CH_2)_q$-pyrimidyl, $-(CH_2)_q$-pyraziqyl, $-(CH_2)_q$-isoxazolyl, $-(CH_2)_q$-oxazolyl, $-(CH_2)_q$-thiazolyl, $-(CH_2)_q$-(1,2,4-oxadiazolyl), $-(CH_2)_q$-imidazolyl, $-(CH_2)_q$-triazolyl and $-(CH_2)_q$-tetrazolyl;

wherein one of the ring nitrogen atoms of said $-(CH_2)_q$-imidazolyl, $-(CH_2)_q$-triazolyl and $-(CH_2)_q$-tetrazolyl may optionally be substituted by $(C_1-C_8)$alkyl optionally independently substituted with one or more halo atoms;

wherein each of said heterocycles may optionally be substituted on one or more of the ring carbon atoms by one or more substituents independently selected from the group consisting of $(C_1-C_8)$alkyl optionally independently substituted with one or more halo atoms, nitro, cyano, $-(CH_2)_q-NG^1G^2$, $-(CH_2)_q-CO_2G^3$, $-(CH_2)_q-CO-NG^1G^2$, $-(CH_2)_q-OG^3$, $-(CH_2)_q-SO_3G^3$, $-(CH_2)_q-SO_2-(C_1-C_6)$alkyl and $-(CH_2)_q-SO_2NG^1G^2$;

wherein the phenyl moiety of said $-(CH_2)_q$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, $-(CH_2)_q-NG^1G^2$, $-(CH_2)_q-CO_2G^3$, $-(CH_2)_q-CO-NG^1G^2$, $-(CH_2)_q-OG^3$, $-(CH_2)_q-SO_3G^3$, $-(CH_2)_q-SO_2-(C_1-C_6)$alkyl, $-(CH_2)_q-SO_2NG^1G^2$; $-(CH_2)_q-NG^3-SO_2-G^3$ and $-(CH_2)_q-NG^3-SO_2-NG^1G^2$;

$Q^4$ is $-(CH_2)_q-CN$, $-(CH_2)_q-CO_2G^3$, $-(CH_2)_q-SO_3G^3$, $-(CH_2)_q-SO_2-(C_1-C_6)$alkyl, $-(CH_2)_q-SO_2NG^1G^2$, $-(CH_2)_qCH_2OH$, $-(CH_2)_q-CHO$, $-(CH_2)_q-CO-G^3$, $-(CH_2)_q-CONG^1G^2$, or a heterocycle selected from $-(CH_2)_q$-thiazolyl, $-(CH_2)_q$-oxazolyl, $-(CH_2)_q$-imidazolyl, $-(CH_2)_q$-triazolyl, $-(CH_2)_q$-1,2,4-oxadiazolyl, $-(CH_2)_q$-isoxazolyl, $-(CH_2)_q$-tetrazolyl and $-(CH_2)_q$-pyrazolyl;

wherein one of the ring nitrogen atoms of said $-(CH_2)_q$-imidazolyl, $-(CH_2)_q$-triazolyl and $-(CH_2)_q$-tetrazolyl may optionally be substituted by $(C_1-C_6)$alkyl optionally independently substituted with one or more halo atoms;

wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, $-(CH_2)_q-CO-NG^1G^2$, $-(CH_2)_q-CO_2G^3$, halo, nitro, cyano, $-(CH_2)_q-CO-NG^1G^2$, $-(CH_2)_q-OG^3$, $-(CH_2)_q-SO_3G^3$, $-(CH_2)_q-SO_2-(C_1-C_6)$alkyl, or $-(CH_2)_q-SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or N—$(C_1-C_6)$alkyl;

$Q^{10}$ is nitro, amino, $(C_2-C_9)$heteroaryl, $(C_2-C_9)$heterocycloalkyl, $(CH_2)_pOR^{11}$, $(CH_2)_qCO_2H$, $(CH_2)_qCOR^{13}$, $(CH_2)_qSO_2NR^{11}R^{12}$, $(CH_2)_q-NR^{11}SO_2R^{10}$, $(CH_2)_qP(O)(OR^8)(OR^9)$, $(CH_2)_q-O-(CH_2)_pCO_2H$, $(CH_2)_q-O-(CH_2)_pCOR^{13}$, $(CH_2)_q-O-(CH_2)_pP(O)(OR^8)(OR^9)$, $(CH_2)_q-O-(CH_2)_pSO_2NR^{11}R^{12}$, or $(CH_2)_q-O-(CH_2)_p-NR^{11}SO_2R^{10}$;

$R^8$ and $R^9$ are each independently hydrogen or $(C_1-C_6)$alkyl; and wherein $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^{10}$ for each occurrence is independently $(C_1-C_6)$alkyl or $(C_1-C_6)$alkoxy$(C_1-C_6)$alkyl;

$R^{11}$ and $R^{12}$ are taken separately and, for each occurrence, are independently hydrogen, $(C_1-C_6)$alkyl, $(C_3-C_8)$cycloalkyl, or $(C_1-C_6)$alkoxy$(C_1-C_6)$alkyl, or $R^{11}$ and $R^{12}$ are taken together with the nitrogen atom to which they are attached and form a pyrrolidine, piperidine or morpholine ring wherein said pyrrolidine, piperidine or morpholine may optionally be substituted at any carbon atom by $(C_1-C_4)$alkyl or $(C_1-C_4)$alkoxy;

$R^{13}$ for each occurrence is independently hydrogen, $(C_1-C_6)$alkyl, $(C_1-C_6)$alkoxy, $NR^{11}R^{12}$, $(C_3-C_8)$cycloalkyl, or $(C_1-C_6)$alkoxy$(C_1-C_6)$alkyl wherein $R^{11}$ and $R^{12}$ are as defined above;

$R^{14}$ and $R^{15}$ are each independently hydrogen, halo, $(C_1-C_6)$alkyl, nitro, cyano, trifluoromethyl, $SO_2R^{10}$, $SO_2NR^{11}R^{12}$, $NR^{11}R^{12}$, $COR^{13}$, $CO_2R^{11}$, $(C_1-C_6)$alkoxy, $NR^{11}SO_2R^{10}$, $NR^{11}COR^{13}$, $NR^{11}CO_2R^{11}$ or $OR^{11}$;

p for each occurrence is independently an integer of 1 to 6; and q for each occurrence is independently 0 or an integer of 1 to 6;

with the proviso that when $Q^9$ is O or S then n is not 0;

with the proviso that when $Q^1$ is oxygen or sulfur then $Q^3$ is absent; and with the proviso that when $Q^2$ is nitrogen then $Q^5$ is absent;

comprising reacting a compound of the formula

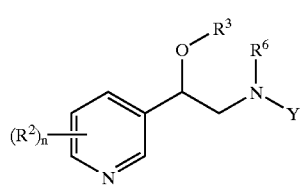

II wherein n, $R^2$, $R^6$ and Y are as defined above; and $R^3$ is tetrahydrofuranyl, tetrahydropyranyl or a silyl protecting group; with tetra-n-butylammonium fluoride.

The present invention further relates to a process wherein a compound of the formula

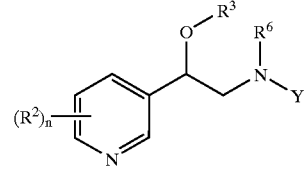

II wherein n, $R^2$, $R^3$, $R^6$ and Y are as defined above, is formed by treating a compound of the formula

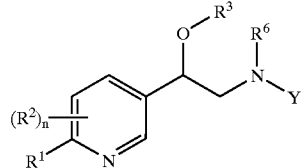

III wherein $R^1$ is halo and wherein n, $R^2$, $R^3$, $R^6$ and Y are as defined above, with ammonium formate in the presence of palladium on carbon.

The present invention further relates to a process wherein a compound of the formula

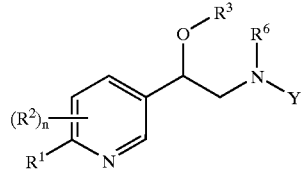

III is formed by reacting a compound of the formula

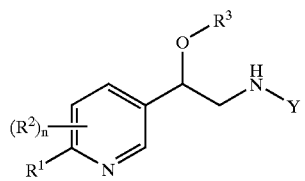

IV wherein $R^1$ is hydrogen or halo and wherein n, $R^2$, $R^3$ and Y are as defined above with an organic acid anhydride, a dicarbonate or an organic acid chloride.

The present invention further relates to a process wherein the dicarbonate is di-tert-butyl dicarbonate The present invention further relates to a process wherein a compound of the formula

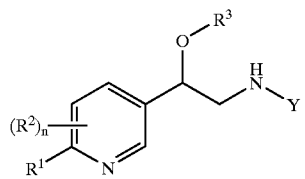

IV is formed by reacting the compound

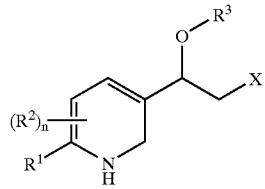
V wherein n, $R^1$, $R^2$, $R^3$ and X are as defined above, with an amine of the formula $H_2NY$, wherein Y is as defined above, in the presence of N,N-diisopropylethylamine.

The present invention relates to a process for preparing a compound of the formula

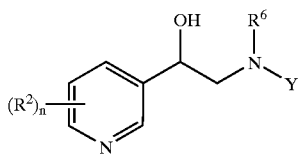
I wherein n is 0, 1, 2 or 3;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ and $NR^4CO_2\ R^4$;

$R^4$ and $R^5$, for each occurrence, are each independently selected from hydrogen, $(C_1-C_{10})$alkyl, $(C_1-C_{10})$alkoxy, $(C_3-C_8)$cycloalkyl,$(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above;

$R^6$ is $COR^7$ or $CO_2R^7$ wherein $R^7$ is $(C_1-C_8)$alkyl; and

Y is

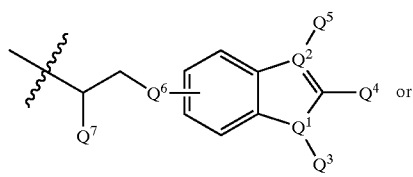
or

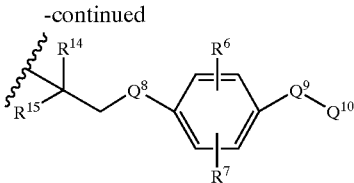

wherein:

$Q^1$ is oxygen, nitrogen or sulfur;

$Q^2$ is carbon or nitrogen;

$Q^3$ is hydrogen, $-(CH_2)_q$-phenyl, $-(C_1-C_{10})$alkyl, $-(CH_2)_q-NG^1G^2$, $-(CH_2)_q-CO_2G^3$, $-(CH_2)_q-CO-NG^1G^2$, $-(CH_2)_q-OG^3$, $-(CH_2)_q-SO_3G^3$, $-(CH_2)_q-SO_2-(C_1-C_6)$alkyl, $-(CH_2)_q-SO_2NG^1G^2$, or a heterocycle selected from the group consisting of $-(CH_2)_q$-pyridyl, $-(CH_2)_q$-pyrimidyl, $-(CH_2)_q$-pyraziqyl, $-(CH_2)_q$-isoxazolyl, $-(CH_2)_q$-oxazolyl, $-(CH_2)_q$-thiazolyl, $-(CH_2)_q$-(1,2,4-oxadiazolyl), $-(CH_2)_q$-imidazolyl, $-(CH_2)_q$-triazolyl and $-(CH_2)_q$-tetrazolyl;

wherein one of the ring nitrogen atoms of said $-(CH_2)_q$-imidazolyl, $-(CH_2)_q$-triazolyl and $-(CH_2)_q$-tetrazolyl may optionally be substituted by $(C_1-C_8)$alkyl optionally independently substituted with one or more halo atoms;

wherein each of said heterocycles may optionally be substituted on one or more of the ring carbon atoms by one or more substituents independently selected from the group consisting of $(C_1-C_8)$alkyl optionally independently substituted with one or more halo atoms, nitro, cyano, $-(CH_2)_q-NG^1G^2$, $-(CH_2)_q-CO_2G^3$, $-(CH_2)_q-CO-NG^1G^2$, $-(CH_2)_q-OG^3$, $-(CH_2)_q-SO_3G^3$, $-(CH_2)_q-SO_2-(C_1-C_6)$alkyl and $-(CH_2)_q-SO_2NG^1G^2$;

wherein the phenyl moiety of said $-(CH_2)_q$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, $-(CH_2)_q-NG^1G^2$, $-(CH_2)_q-CO_2G^3$, $-(CH_2)_q-CO-NG^1G^2$, $-(CH_2)_q-OG^3$, $-(CH_2)_q-SO_3G^3$, $-(CH_2)_q-SO_2-(C_1-C_6)$alkyl, $-(CH_2)_q-SO_2NG^1G^2$; $-(CH_2)_q-NG^3-SO_2-G^3$ and $-(CH_2)_q-NG^3-SO_2-NG^1G^2$;

$Q^4$ is $-(CH_2)_q-CN$, $-(CH_2)_qCO_2G^3$, $-(CH_2)_q-SO_3G^3$, $-(CH_2)_q-SO_2-(C_1-C_6)$alkyl, $-(CH_2)_q-SO_2NG^1G^2$, $-(CH_2)_qCH_2OH$, $-(CH_2)_q-CHO$, $-(CH_2)_q-CO-G^3$, $-(CH_2)_q-CONG^1G^2$, or a heterocycle selected from $-(CH_2)_q$-thiazolyl, $-(CH_2)_q$-oxazolyl, $-(CH_2)_q$-imidazolyl, $-(CH_2)_q$-triazolyl, $-(CH_2)_q$-1,2,4-oxadiazolyl, $-(CH_2)_q$-isoxazolyl, $-(CH_2)_q$-tetrazolyl and $-(CH_2)_q$-pyrazolyl;

wherein one of the ring nitrogen atoms of said $-(CH_2)_q$-imidazolyl, $-(CH_2)_q$-triazolyl and $-(CH_2)_q$-tetrazolyl may optionally be substituted by $(C_1-C_6)$alkyl optionally independently substituted with one or more halo atoms;

wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, —(CH$_2$)$_q$—CO—NG$^1$G$^2$, —(CH$_2$)$_q$—CO$_2$G$^3$, halo, nitro, cyano, —(CH$_2$)$_q$—CO—NG$^1$G$^2$, —(CH$_2$)$_q$—OG$^3$, —(CH$_2$)$_q$—SO$_3$G$^3$, —(CH$_2$)$_q$—SO$_2$—(C$_1$–C$_6$)alkyl, or —(CH$_2$)$_q$—SO$_2$NG$^1$G$^2$;

Q$^5$ is hydrogen or (C$_1$–C$_6$)alkyl optionally independently substituted with one or more halo atoms;

Q$^6$ is a covalent bond, oxygen or sulfur;

Q$^7$ is hydrogen or (C$_1$–C$_6$)alkyl optionally independently substituted with one or more halo atoms;

Q$^8$ and Q$^9$ are independently a covalent bond, oxygen, sulfur, NH or N—(C$_1$–C$_6$)alkyl;

Q$^{10}$ is nitro, amino, (C$_2$–C$_9$)heteroaryl, (C$_2$–C$_9$)heterocycloalkyl, (CH$_2$)$_p$OR$^{11}$, (CH$_2$)$_q$CO$_2$H, (CH$_2$)$_q$COR$^{13}$, (CH$_2$)$_q$SO$_2$NR$^{11}$R$^{12}$, (CH$_2$)$_q$NR$^{11}$SO$_2$R$^{10}$, (CH$_2$)$_q$P(O)(OR$^8$)(OR$^9$), (CH$_2$)$_q$—O—(CH$_2$)$_p$CO$_2$H, (CH$_2$)$_q$—O—(CH$_2$)$_p$COR$^{13}$, (CH$_2$)$_q$—O—(CH$_2$)$_p$P(O)(OR$^8$)(OR$^9$), (CH$_2$)$_q$—O—(CH$_2$)$_p$SO$_2$NR$^{11}$R$^{12}$, or (CH$_2$)$_q$—O—(CH$_2$)$_p$—NR$^{11}$SO$_2$R$^{10}$;

R$^8$ and R$^9$ are each independently hydrogen or (C$_1$–C$_6$)alkyl; and wherein G$^1$ and G$^2$ for each occurrence are each independently hydrogen, (C$_1$–C$_6$)alkyl optionally independently substituted with one or more halo, (C$_1$–C$_8$)alkoxy(C$_1$–C$_6$)alkyl or (C$_3$–C$_8$)cycloalkyl, or G$^1$ and G$^2$ together with the nitrogen to which they are attached form a saturated heterocyclic ring having from 3 to 7 carbon atoms wherein one of said carbon atoms may optionally be replaced by oxygen, nitrogen or sulfur;

G$^3$ for each occurrence is independently hydrogen or (C$_1$–C$_6$)alkyl;

R$^{10}$ for each occurrence is independently (C$_1$–C$_6$)alkyl or (C$_1$–C$_6$)alkoxy(C$_1$–C$_6$)alkyl;

R$^{11}$ and R$^{12}$ are taken separately and, for each occurrence, are independently hydrogen, (C$_1$–C$_6$)alkyl, (C$_3$–C$_8$)cycloalkyl, or (C$_1$–C$_6$)alkoxy(C$_1$–C$_6$)alkyl, or R$^{11}$ and R$^{12}$ are taken together with the nitrogen atom to which they are attached and form a pyrrolidine, piperidine or morpholine ring wherein said pyrrolidine, piperidine or morpholine may optionally be substituted at any carbon atom by (C$_1$–C$_4$)alkyl or (C$_1$–C$_4$)alkoxy;

R$^{13}$ for each occurrence is independently hydrogen, (C$_1$–C$_6$)alkyl, (C$_1$–C$_6$)alkoxy, NR$^{11}$R$^{12}$, (C$_3$–C$_8$)cycloalkyl, or (C$_1$–C$_6$)alkoxy(C$_1$–C$_6$)alkyl wherein R$^{11}$ and R$^{12}$ are as defined above;

R$^{14}$ and R$^{15}$ are each independently hydrogen, halo, (C$_1$–C$_6$)alkyl, nitro, cyano, trifluoromethyl, SO$_2$R$^{10}$, SO$_2$NR$^{11}$R$^{12}$, NR$^{11}$R$^{12}$, COR$^{13}$, CO$_2$R$^{11}$, (C$_1$–C$_6$)alkoxy, NR$^{11}$SO$_2$R$^{10}$, NR$^{11}$COR$^{13}$, NR$^{11}$CO$_2$R$^{11}$ or OR$^{11}$;

p for each occurrence is independently an integer of 1 to 6; and q for each occurrence is independently 0 or an integer of 1 to 6;

with the proviso that when Q$^9$ is O or S then n is not 0;

with the proviso that when Q$^1$ is oxygen or sulfur then Q$^3$ is absent; and with the proviso that when Q$^2$ is nitrogen then Q$^5$ is absent;

comprising (a) reacting a compound of the formula

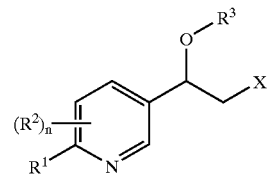

V wherein R$^1$ is hydrogen or halo, and n, R$^1$, R$^2$, R$^3$ and X are as defined above, with an amine of the formula H$_2$NY, wherein Y is as defined above in the presence of N,N-diisopropylethylamine;

(b) reacting the compound of formula IV so formed

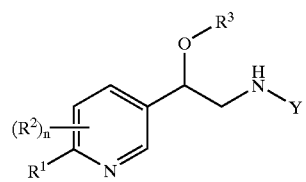

IV wherein R$^1$ is hydrogen or halo and wherein n, R$^2$, R$^3$ and Y are as defined above with an organic acid anhydride, a dicarbonate or an organic acid chloride, to form a compound of the formula

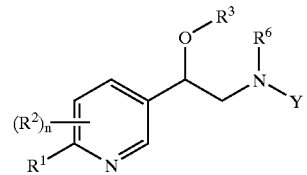

III (c) treating the compound of formula III, wherein R$^1$ is halo, so formed in step (b) with ammonium formate in the presence of palladium-on-carbon to form the compound of the formula

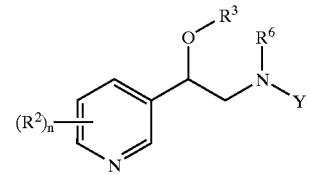

II wherein n, R$^2$, R$^3$, R$^6$ and Y are as defined above, and (d) treating the compound of formula II so formed with tetra-n-butylammonium fluoride.

The present invention relates to a process for preparing a compound of the formula

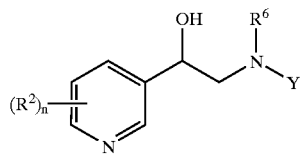

wherein n is 0, 1, 2 or 3;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ and $NR^4CO_2R^4$;

$R^4$ and $R^5$, for each occurrence, are each independently selected from hydrogen, $(C_1-C_{10})$alkyl, $(C_1-C_{10})$alkoxy, $(C_3-C_8)$cycloalkyl, $(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above;

$R^6$ is $COR^7$ or $CO_2R^7$ wherein $R^7$ is $(C_1-C_8)$alkyl; and Y is

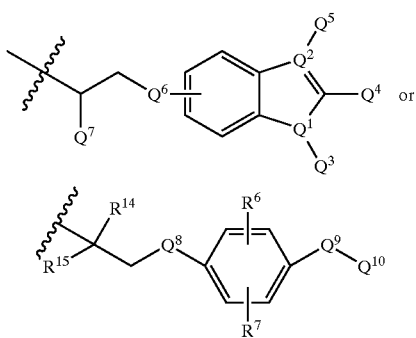

wherein:

$Q^1$ is oxygen, nitrogen or sulfur;

$Q^2$ is carbon or nitrogen;

$Q^3$ is hydrogen, —$(CH_2)_q$-phenyl, —$(C_1-C_{10})$alkyl, —$(CH_2)_q$—$NG^1G^2$, —$(CH_2)_q$—$CO_2G_3$, —$(CH_2)_q$—CO—$NG^1G^2$, —$(CH_2)_q$—$OG^3$, —$(CH_2)_q$—$SO_3G^3$, —$(CH_2)_q$—$SO_2$—$(C_1-C_6)$alkyl, —$(CH_2)_q$—$SO_2NG^1G^2$, or a heterocycle selected from —$(CH_2)_q$-pyridyl, —$(CH_2)_q$-pyrimidyl, —$(CH_2)_q$-pyraziqyl, —$(CH_2)_q$-isoxazolyl, —$(CH_2)_q$-oxazolyl, —$(CH_2)_q$-thiazolyl, —$(CH_2)_q$-(1,2,4-oxadiazolyl), —$(CH_2)_q$-imidazolyl, —$(CH_2)_q$-triazolyl and —$(CH_2)_q$-tetrazolyl;

wherein one of the ring nitrogen atoms of said —$(CH_2)_q$-imidazolyl, —$(CH_2)_q$-triazolyl and —$(CH_2)_q$-tetrazolyl may optionally be substituted by $(C_1-C_8)$alkyl optionally independently substituted with one or more halo atoms;

wherein each of said heterocycles may optionally be substituted on one or more of the ring carbon atoms by one or more substituents independently selected from the group consisting of $(C_1-C_8)$alkyl optionally independently substituted with one or more halo atoms, nitro, cyano, —$(CH_2)_q$—$NG^1G^2$, —$(CH_2)_q$—$CO_2G^3$, —$(CH_2)_q$—CO—$NG^1G^2$, —$(CH_2)_q$—$OG^3$, —$(CH_2)_q$—$SO_3G^3$, —$(CH_2)_q$—$SO_2$—$(C_1-C_6)$alkyl and —$(CH_2)_q$—$SO_2NG^1G^2$;

wherein the phenyl moiety of said —$(CH_2)_q$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, —$(CH_2)_q$—$NG^1G^2$, —$(CH_2)_q$—$CO_2G^3$, —$(CH_2)_q$—CO—$NG^1G^2$, —$(CH_2)_q$—$OG^3$, —$(CH_2)_q$—$SO_3G^3$, —$(CH_2)_q$—$SO_2$—$(C_1-C_6)$alkyl, —$(CH_2)_q$—$SO_2NG^1G^2$; —$(CH_2)_q$—$NG^3SO_2G^3$ and —$(CH_2)_q$—$NG^3SO_2$—$NG^1G^2$;

$Q^4$ is —$(CH_2)_q$—CN, —$(CH_2)_q$—$CO_2G^3$, —$(CH_2)_q$—$SO_3G^3$, —$(CH_2)_q$—$SO_2$—$(C_1-C_6)$alkyl, —$(CH_2)_q$—$SO_2NG^1G^2$, —$(CH_2)_qCH_2OH$, —$(CH_2)_qCHO$, —$(CH_2)_q$—CO—$G^3$, —$(CH_2)_q$—$CONG^1G^2$, or a heterocycle selected from —$(CH_2)_q$-thiazolyl, —$(CH_2)_q$-oxazolyl, —$(CH_2)_q$-imidazolyl, —$(CH_2)_q$-triazolyl, —$(CH_2)_q$-1,2,4-oxadiazolyl, —$(CH_2)_q$-isoxazolyl, —$(CH_2)_q$-tetrazolyl and —$(CH_2)_q$-pyrazolyl;

wherein one of the ring nitrogen atoms of said —$(CH_2)_q$-imidazolyl, —$(CH_2)_q$-triazolyl and —$(CH_2)_q$-tetrazolyl may optionally be substituted by $(C_1-C_6)$alkyl optionally independently substituted with one or more halo atoms;

wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, —$(CH_2)_q$—CO—$NG^1G^2$, —$(CH_2)_q$—$CO_2G^3$, halo, nitro, cyano, —$(CH_2)_q$—CO—$NG^1G^2$, —$(CH_2)_q$—$OG^3$, —$(CH_2)_q$—$SO_3G^3$, —$(CH_2)_q$—$SO_2$$(C_1-C_6)$alkyl, or —$(CH_2)_q$—$SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or N—$(C_1-C_6)$alkyl;

$Q^{10}$ is nitro, amino, $(C_2-C_9)$heteroaryl, $(C_2-C_9)$heterocycloalkyl, $(CH_2)_pOR^{11}$, $(CH_2)_qCO_2H$, $(CH_2)_qCOR^{13}$, $(CH_2)_qSO_2NR^{11}R^{12}$, $(CH_2)_q$—$NR^{11}SO_2R^{10}$, $(CH_2)_qP(O)(OR^8)(OR^9)$, $(CH_2)_q$—O—$(CH_2)_pCO_2H$, $(CH_2)_q$—O—$(CH_2)_pCOR^{13}$, $(CH_2)_q$—O—$(CH_2)_pP(O)(OR^8)(OR^9)$, $(CH_2)_q$—O—$(CH_2)_pSO_2NR^{11}R^{12}$, or $(CH_2)_q$—O—$(CH_2)_p$—$NR^{11}SO_2R^{10}$;

$R^8$ and $R^9$ are each independently hydrogen or $(C_1-C_6)$alkyl; and wherein $G^1$ and $G^2$ for each occurrence are each independently hydrogen, $(C_1-C_6)$alkyl optionally independently substituted with one or more halo, $(C_1-C_8)$ alkoxy($C_1$–$C_6$)alkyl or ($C_3$–$C_8$)cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or ($C_1$–$C_6$)alkyl;

$R^{10}$ for each occurrence is independently ($C_1$–$C_6$)alkyl or ($C_1$–$C_6$)alkoxy($C_1$–$C_6$)alkyl;

$R^{11}$ and $R^{12}$ are taken separately and, for each occurrence, are independently hydrogen, ($C_1$–$C_6$)alkyl, ($C_3$–$C_8$)cycloalkyl, or ($C_1$–$C_6$)alkoxy($C_1$–$C_6$)alkyl, or $R^{11}$ and $R^{12}$ are taken together with the nitrogen atom to which they are attached and form a pyrrolidine, piperidine or morpholine ring wherein said pyrrolidine, piperidine or morpholine may optionally be substituted at any carbon atom by ($C_1$–$C_4$)alkyl or ($C_1$–$C_4$)alkoxy;

$R^{13}$ for each occurrence is independently hydrogen, ($C_1$–$C_6$)alkyl, ($C_1$–$C_6$)alkoxy, $NR^{11}R^{12}$, ($C_3$–$C_8$)cycloalkyl, or ($C_1$–$C_6$)alkoxy($C_1$–$C_6$)alkyl wherein $R^{11}$ and $R^{12}$ are as defined above;

$R^{14}$ and $R^{15}$ are each independently hydrogen, halo, ($C_1$–$C_6$)alkyl, nitro, cyano, trifluoromethyl, $SO_2R^{10}$, $SO_2NR^{11}R^{12}$, $NR^{11}R^{12}$, $COR^{13}$, $CO_2R^{11}$, ($C_1$–$C_6$)alkoxy, $NR^{11}SO_2R^{10}$, $NR^{11}COR^{13}$, $NR^{11}CO_2R^{11}$ or $OR^{11}$;

p for each occurrence is independently an integer of 1 to 6; and q for each occurrence is independently 0 or an integer of 1 to 6;

with the proviso that when $Q^9$ is O or S then n is not 0;

with the proviso that when $Q^1$ is oxygen or sulfur then $Q^3$ is absent; and with the proviso that when $Q^2$ is nitrogen then $Q^5$ is absent;

comprising reacting a compound of the formula

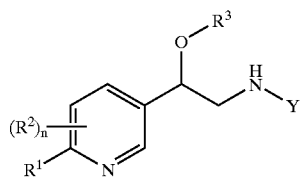

IV wherein $R^1$ is halo and wherein n, $R^2$, $R^3$ and Y are as defined above, with ammonium formate in the presence of palladium-on-carbon.

The present invention further relates to a process wherein a compound of the formula

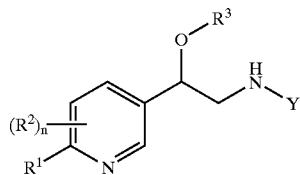

IV is formed by reacting a compound of the formula

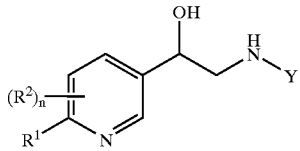

VII wherein $R^1$ is hydrogen or halo, and wherein n, $R^2$ and Y are as defined above, with an organic acid anhydride, a dicarbonate or an organic acid chloride.

The present invention further relates to a process wherein the dicarbonate is di-tert-butyl dicarbonate The present invention further relates to a process wherein the compound of the formula

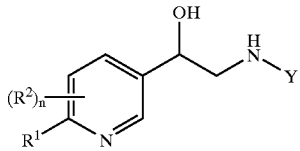

VII is formed by reacting the compound

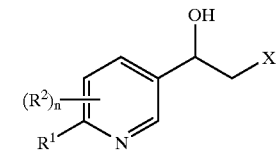

VIII wherein n, $R^1$, $R^2$ and X are as defined above, with an amine of the formula $H_2NY$, wherein Y is as defined above, in the presence of N,N-diisopropylethylamine.

This invention relates to a process for preparing a compound of the formula

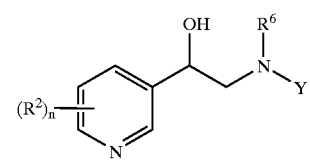

I wherein n is 0, 1, 2 or 3;

each $R^2$ is independently hydrogen, halo, trifluoromethyl, cyano, $SR^4$, $OR^4$, $SO_2R^4$, $OCOR^5$, or ($C_1$–$C_{10}$)alkyl wherein the alkyl group is optionally substituted by hydroxy, halo, cyano, $N(R^4)_2$, $SR^4$, trifluoromethyl, $OR^4$, ($C_3$–$C_8$)cycloalkyl, ($C_6$–$C_{10}$)aryl, $NR^4COR^5$, $COR^5$, $SO_2R^5$, $OCOR^5$, $NR^4SO_2R^5$ and $NR^4CO_2R^4$;

$R^4$ and $R^5$, for each occurrence, are each independently selected from hydrogen, ($C_1$–$C_{10}$)alkyl, ($C_1$–$C_{10}$)alkoxy, ($C_3$–$C_8$)cycloalkyl,($C_6$–$C_{10}$)aryl, ($C_2$–$C_9$)heterocycloalkyl, ($C_2$–$C_9$)heteroaryl or ($C_1$–$C_6$)aryl wherein the alkyl group is optionally substituted by the group consisting of hydroxy, halo, carboxy, ($C_1$–$C_{10}$)alkyl-$CO_2$, ($C_1$–$C_{10}$)alkylsulfonyl, ($C_3$–$C_8$)cycloalkyl, ($C_1$–$C_{10}$)alkoxy, or ($C_1$–$C_6$)alkyl; and wherein the aryl, heterocycloalkyl and heteroaryl groups are optionally substituted by one to four groups consisting of halo, nitro, oxo, $((C_1-C_6)alkyl)_2amino$, pyrrolidine, piperidine, $(C_1-C_{10})alkyl$, $(C_1-C_{10})alkoxy$, $(C_1-C_{10})alkylthio$ and $(C_1-C_{10})alkyl$ wherein the alkyl group is optionally substituted by one to four groups selected from hydroxy, halo, carboxy, $(C_1-C_6)$ alkyl-$CO_2$, $(C_1-C_6)alkylsulfonyl$, $(C_3-C_8)cycloalkyl$ and $(C_1-C_6)alkoxy$;

or $R^5$ is $N(R^4)_2$ wherein $R^4$ is as defined above;

$R^6$ is $COR^7$ or $CO_2R^7$ wherein $R^7$ is $(C_1-C_8)alkyl$; and Y is

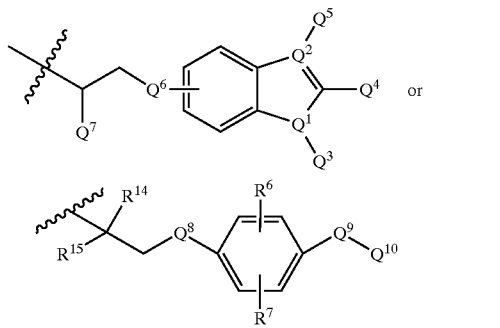

wherein:

$Q^1$ is oxygen, nitrogen or sulfur;

$Q^2$ is carbon or nitrogen;

$Q^3$ is hydrogen, $—(CH_2)_q$-phenyl, $—(C_1-C_{10})alkyl$, $—(CH_2)_q—NG^1G^2$, $—(CH_2)_q—CO_2G^3$, $—(CH_2)_qCO—NG^1G^2$, $—(CH_2)_q—OG^3$, $—(CH_2)_q—SO_3G^3$, $—(CH_2)_q—SO_2—(C_1-C_6)alkyl$, $—(CH_2)_q—SO_2NG^1G^2$, or a heterocycle selected from the group consisting of $—(CH_2)_q$-pyridyl, $—(CH_2)_q$-pyrimidyl, $—(CH_2)_q$-pyraziqyl, $—(CH_2)_q$-isoxazolyl, $—(CH_2)_q$-oxazolyl, $—(CH_2)_q$-thiazolyl, $—(CH_2)_q$-(1,2,4-oxadiazolyl), $—(CH_2)_q$-imidazolyl, $—(CH_2)_q$-triazolyl and $—(CH_2)_q$-tetrazolyl;

wherein one of the ring nitrogen atoms of said $—(CH_2)_q$-imidazolyl, $—(CH_2)_q$-triazolyl and $—(CH_2)_q$-tetrazolyl may optionally be substituted by $(C_1-C_8)alkyl$ optionally independently substituted with one or more halo atoms;

wherein each of said heterocycles may optionally be substituted on one or more of the ring carbon atoms by one or more substituents independently selected from the group consisting of $(C_1-C_8)alkyl$ optionally independently substituted with one or more halo atoms, nitro, cyano, $—(CH_2)_q—NG^1G^2$, $—(CH_2)_q—CO_2G^3$, $—(CH_2)_q—CO—NG^1G^2$, $—(CH_2)_q—OG^3$, $—(CH_2)_q—SO_3G^3$, $—(CH_2)_q—SO_2—(C_1-C_6)alkyl$ and $—(CH_2)_q—SO_2NG^1G^2$;

wherein the phenyl moiety of said $—(CH_2)_q$-phenyl may optionally be substituted with one or more substituents independently selected from the group consisting of $(C_1-C_6)alkyl$ optionally independently substituted with one or more halo atoms, hydroxy, $(C_1-C_6)alkoxy$ optionally independently substituted with one or more halo atoms, $(C_1-C_6)alkylthio$, fluoro, chloro, bromo, iodo, cyano, nitro, $—(CH_2)_q—NG^1G^2$, $—(CH_2)_q—CO_2G^3$, $—(CH_2)_q—CO—NG^1G^2$, $—(CH_2)_q—OG^3$, $—(CH_2)_q—SO_3G^3$, $—(CH_2)_q—SO_2(C_1-C_6)alkyl$, $—(CH_2)_q—SO_2NG^1G^2$; $—(CH_2)_q—NG^3—SO_2—G^3$ and $—(CH_2)_q—NG^3—SO_2—NG^1G^2$;

$Q^4$ is $—(CH_2)_q—CN$, $—(CH_2)_qCO_2G^3$, $—(CH_2)_q—SO_3G^3$, $—(CH_2)_q—SO_2—(C_1-C_6)alkyl$, $—(CH_2)_q—SO_2NG^1G^2$, $—(CH_2)_qCH_2OH$, $—(CH_2)_q—CHO$, $—(CH_2)_q—CO—G^3$, $—(CH_2)_q—CONG^1G^2$; or a heterocycle selected from $—(CH_2)_q$-thiazolyl, $—(CH_2)_q$-oxazolyl, $—(CH_2)_q$-imidazolyl, $—(CH_2)_q$-triazolyl, $—(CH_2)_q$-1,2,4-oxadiazolyl, $—(CH_2)_q$-isoxazolyl, $—(CH_2)_q$-tetrazolyl and $—(CH_2)_q$-pyrazolyl;

wherein one of the ring nitrogen atoms of said $—(CH_2)_q$-imidazolyl, $—(CH_2)_q$-triazolyl and $—(CH_2)_q$-tetrazolyl may optionally be substituted by $(C_1-C_6)alkyl$ optionally independently substituted with one or more halo atoms;

wherein each of said heterocycles may optionally be substituted on one or more of the ring carbon atoms by one or more substituents independently selected from the group consisting of hydrogen, $(C_1-C_6)alkyl$ optionally independently substituted with one or more halo atoms, $—(CH_2)_q—CO—NG^1G^2$, $—(CH_2)_q—CO_2G^3$, halo, nitro, cyano, $—(CH_2)_q—CO—NG^1G^2$, $—(CH_2)_q—OG^3$, $—(CH_2)_q—SO_3G^3$, $—(CH_2)_q—SO_2—(C_1-C_6)alkyl$, or $—(CH_2)_q—SO_2NG^1G^2$;

$Q^5$ is hydrogen or $(C_1-C_6)alkyl$ optionally independently substituted with one or more halo atoms;

$Q^6$ is a covalent bond, oxygen or sulfur;

$Q^7$ is hydrogen or $(C_1-C_6)alkyl$ optionally independently substituted with one or more halo atoms;

$Q^8$ and $Q^9$ are independently a covalent bond, oxygen, sulfur, NH or N—$(C_1-C_6)alkyl$;

$Q^{10}$ is $(CH_2)_pOR^{11}$, $(CH_2)_qCO_2H$, $(CH_2)_qCOR^{13}$, $(CH_2)_qSO_2NR^{11}R^{12}$, $(CH_2)_q—NR^{11}SO_2R^{10}$, $(CH_2)_qP(O)(OR^8)(OR^9)$, $(CH_2)_q—O—(CH_2)_pCO_2H$, $(CH_2)_q—O—(CH_2)_pCOR^{13}$, $(CH_2)_q—O—(CH_2)_pP(O)(OR^8)(OR^9)$, $(CH_2)_q—O—(CH_2)_pSO_2NR^{11}R^{12}$, or $(CH_2)_q—O—(CH_2)_p—NR^{11}SO_2R^{10}$;

$R^8$ and $R^9$ are each independently hydrogen or $(C_1-C_6)alkyl$; and wherein $G^1$ and $G^2$ for each occurrence are each independently hydrogen, $(C_1-C_6)alkyl$ optionally independently substituted with one or more halo, $(C_1-C_8)alkoxy(C_1-C_6)alkyl$ or $(C_3-C_8)cycloalkyl$, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)alkyl$;

$R^{10}$ for each occurrence is independently $(C_1-C_6)alkyl$ or $(C_1-C_6)alkoxy(C_1-C_6)alkyl$;

$R^{11}$ and $R^{12}$ are taken separately and, for each occurrence, are independently hydrogen, $(C_1-C_6)alkyl$, $(C_3-C_8)cycloalkyl$, or $(C_1-C_6)alkoxy(C_1-C_6)alkyl$, or $R^{11}$ and $R^{12}$ are taken together with the nitrogen atom to which they are attached and form a pyrrolidine, piperidine or morpholine ring wherein said pyrrolidine, piperidine or morpholine may optionally be substituted at any carbon atom by $(C_1-C_4)alkyl$ or $(C_1-C_4)alkoxy$;

$R^{13}$ for each occurrence is independently hydrogen, $(C_1-C_6)alkyl$, $(C_1-C_6)alkoxy$, $NR^{11}R^{12}$, $(C_3-C_8)cycloalkyl$, or $(C_1-C_6)alkoxy(C_1-C_6)alkyl$ wherein $R^{11}$ and $R^{12}$ are as defined above;

$R^{14}$ and $R^{15}$ are each independently hydrogen, halo, $(C_1-C_6)alkyl$, nitro, cyano, trifluoromethyl, $SO_2R^{10}$, $SO_2NR^{11}R^{12}$, $NR^{11}R^{12}$, $COR^{13}$, $CO_2R^{11}$, $(C_1-C_6)alkoxyl$, $NR^{11}SO_2R^{10}$, $NR^{11}COR^{13}$, $NR^{11}CO_2R^{11}$ or $OR^{11}$;

p for each occurrence is independently an integer of 1 to 6; and q for each occurrence is independently 0 or an integer of 1 to 6;

with the proviso that when $Q^9$ is O or S then n is not 0;

with the proviso that when $Q^1$ is oxygen or sulfur then $Q^3$ is absent; and with the proviso that when $Q^2$ is nitrogen then $Q^5$ is absent;

comprising (a) reacting the compound of the formula

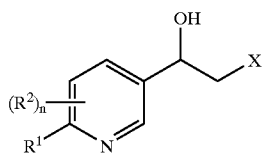

VIII wherein $R^1$ is hydrogen or halo, and n, $R^1$, $R^2$, $R^3$ and X are as defined above, with an amine of the formula $H_2NY$, wherein Y is as defined above, in the presence of N,N-diisopropylethylamine;

(b) reacting the compound of the formula VII so formed

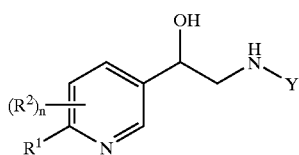

VII wherein $R^1$ is hydrogen or halo and wherein n, $R^2$ and Y are as defined above with an organic acid anhydride, a dicarbonate or an organic acid chloride to form a compound of the formula

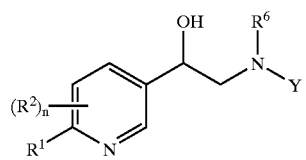

VI wherein n, $R^1$, $R^2$, $R^6$ and Y are as defined above and (c) reacting the compound of formula VI, wherein $R^1$ is halo, so formed with ammonium formate in the presence of palladium-on-carbon.

This invention relates to a process for preparing a compound of the formula

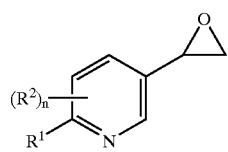

XX wherein n is 0, 1, 2 or 3;

$R^1$ is hydrogen or halo;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR_4SO_2R^5$ and $NR^4CO_2R^4$;

$R^4$ and $R^5$, for each occurrence, are each independently selected from hydrogen, $(C_1-C_{10})$alkyl, $(C_1-C_{10})$alkoxy, $(C_3-C_8)$cycloalkyl,$(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, and or $(C_1-C_6)$alkyl; and wherein the aryl, heterocycloalkyl and heteroaryl groups are optionally substituted by one to four groups consisting of halo, nitro, oxo, $((C_1-C_6)alkyl)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above;

comprising reacting a compound of the formula

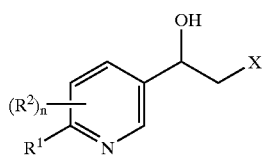

X wherein n, $R^1$, $R^2$ and X are as defined above, with a non-nucleophilic base.

The present invention further relates to a process wherein the non-nucleophilic base is sodium hydroxide, potassium hydroxide, sodium hydride, potassium tert-butoxide or 1,8-diazabicyclo[5.4.0]undec-7-ene.

This invention relates to a compound of the formula

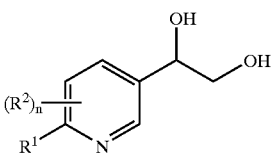

XI wherein n is 0, 1, 2 or 3;

$R^1$ is hydrogen or halo;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ and $NR^4CO_2R^4$;

$R^4$ and $R^5$, for each occurrence, are each independently selected from hydrogen, $(C_1-C_{10})$alkyl, $(C_1-C_{10})$alkoxy, $(C_3-C_8)$cycloalkyl,$(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)alkyl)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above.

The present invention further relates to a compound wherein the compound of formula XI is the R enantiomer

XI wherein $R^1$ is chloro and $R^2$ is hydrogen.

The present invention further relates to a compound wherein the compound of formula XI is the R enantiomer

XI wherein $R^1$ and $R^2$ are hydrogen.

This invention relates to a compound of the formula

XV wherein n is 0, 1, 2 or 3;

$R^1$ is hydrogen or halo;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ and $NR^4CO_2R^4$;

$R^4$ and $R^5$, for each occurrence, are each independently selected from hydrogen, $(C_1-C_{10})$alkyl, $(C_1-C_{10})$alkoxy, $(C_3-C_8)$cycloalkyl,$(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above.

The present invention further relates to a compound wherein the compound of formula XI is the R enantiomer

XV wherein $R^1$ is chloro and $R^2$ is hydrogen.

The present invention further relates to a compound wherein the compound of formula XI is the R enantiomer

XV wherein $R^1$ and $R^2$ are hydrogen.

This invention relates to a compound of the formula

IX wherein n is 0, 1, 2 or 3;

$R^1$ is hydrogen or halo;

each $R^2$ is independently hydrogen, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$aryl, $NR^4COR^5$, $COR^5$, $SO_2R^5$, $OCOR^5$, $NR^4SO_2R^5$ and $NR^4CO_2R^4$;

$R^3$ is tetrahydrofuranyl, tetrahydropyranyl or a silyl protetcting group;

X is halo, methanesulfonyloxy, benzenesulfonyloxy, p-toluenesulfonyloxy, m-nitrobenzenesulfonyloxy or p-nitrobenzenexulfonyloxy;

$R^4$ and $R^5$, for each occurrence, are each independently selected from hydrogen, $(C_1-C_{10})$alkyl, $(C_1-C_{10})$alkoxy,$(C_3-C_8)$cycloalkyl,$(C_6-C_{10})$aryl, $(C_2-C_9)$heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above.

The present invention further relates to a compound wherein the compound of formula IX is the R enantiomer

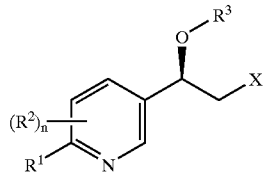

wherein $R^1$ is chloro; $R^2$ is hydrogen; $R^3$ is tert-butyldimethylsilyl; and X is p-toluenesulfonyloxy.

The present invention further relates to a compound wherein the compound of formula IX is the R enantiomer

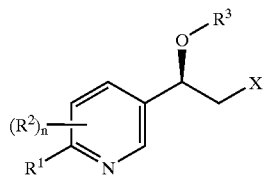

wherein $R^1$ and $R^2$ are hydrogen.

This invention relates to a compound of the formula

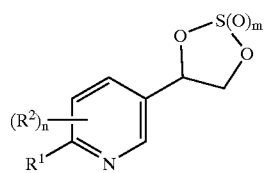

XVII wherein n is 0, 1, 2 or 3;
  m is 1 or 2;
  $R^1$ is hydrogen or halo;
  each $R^2$ is independently hydrogen, nitro, halo, trifluoromethyl, cyano, $SR^4$, $OR^4$, $SO_2R^4$, $OCOR^5$, or $(C_1-C_{10})$alkyl wherein the alkyl group is optionally substituted by hydroxy, halo, cyano, $N(R^4)_2$, $SR^4$, trifluoromethyl, $OR^4$, $(C_3-C_8)$cycloalkyl, $(C_6-C_{10})$ aryl, $NR^4COR^5$, $COR^5$, $SO_2R^5$, $OCOR^5$, $NR^4SO_2R^5$ and $NR^4CO_2 R^4$;
  $R^4$ and $R^5$, for each occurrence, are each independently selected from hydrogen, $(C_1-C_{10})$alkyl, $(C_1-C_{10})$ alkoxy, $(C_3-C_8)$cycloalkyl,$(C_6-C_{10})$aryl, $(C_2-C_9)$ heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$ alkyl-$CO_2$, $(C_1-C_{10})$alkylsulfonyl, $(C_3-C_8)$cycloalkyl, $(C_1-C_{10})$alkoxy, or $(C_1-C_6)$alkyl; and
  wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$ alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$ alkyl-$CO_2$, $(C_1-C_6)$alkylsulfonyl, $(C_3-C_8)$cycloalkyl and $(C_1-C_6)$alkoxy;
  or $R^5$ is $N(R^4)_2$ wherein $R^4$ is as defined above.

The present invention further relates to a compound wherein m is 2, $R^1$ is chloro, and $R^2$ is hydrogen.

The present invention further relates to a compound wherein m is 2 and $R^2$ and $R^3$ are hydrogen.

The present invention further relates to a compound wherein the compound of formula XVII is the R enantiomer

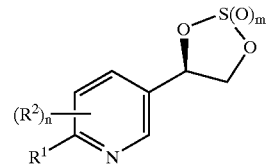

XVII wherein m is 2 and $R^1$ and $R^2$ are hydrogen.

The present invention further relates to a compound wherein the compound of formula XVII is the R enantiomer

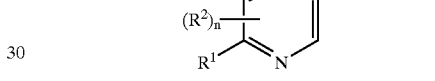

XVII wherein m is 2, $R^1$ is chloro and $R^2$ are hydrogen.

This invention relates to a compound of the formula

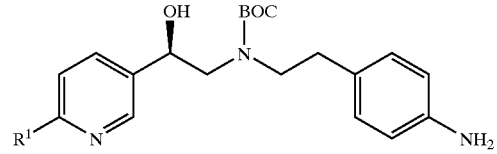

XVIII wherein $R^1$ is hydrogen or chloro and BOC is tert-butoxycarbonyl.

This invention relates to a compound of the formula

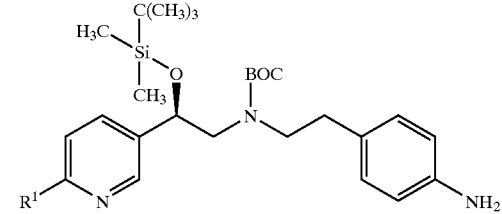

XIX wherein $R^1$ is hydrogen or chloro and BOC is tert-butoxycarbonyl.

This invention relates to a compound of the formula

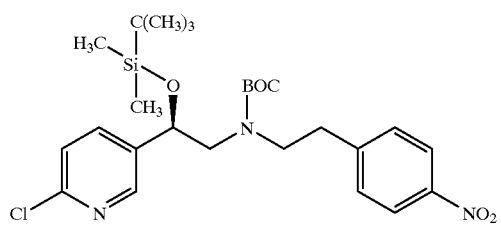

XXI wherein BOC is tert-butoxycarbonyl.

This invention relates to a compound of the formula

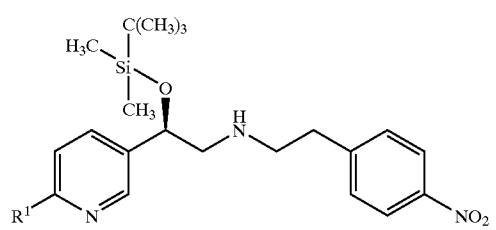

XXII wherein $R^1$ is hydrogen or chloro.

DETAILED DESCRIPTION OF THE INVENTION

The following reaction Scheme illustrates the preparation of the compounds of the present invention. Unless otherwise indicated n, $R^1$, $R^2$, $R^3$, $R^6$, X and Y in the reaction Schemes and the discussion that follow are defined as above.

Preparation A

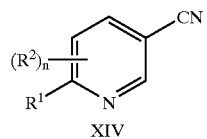

XIV

↓1

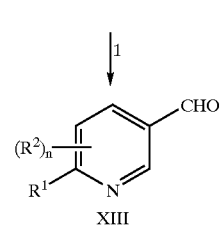

XIII

↓2

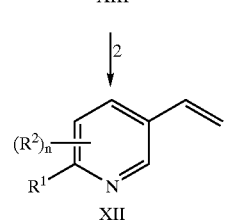

XII

↓3

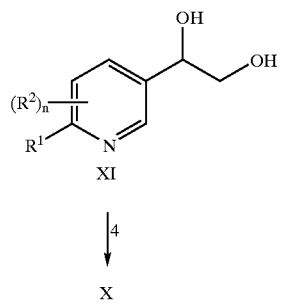

XI

↓4

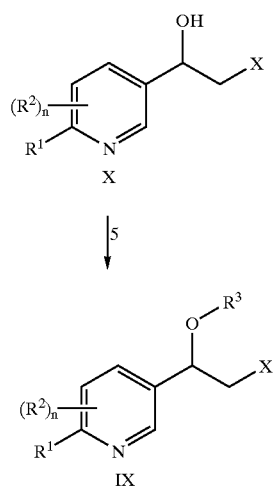

X

↓5

IX

Scheme 1

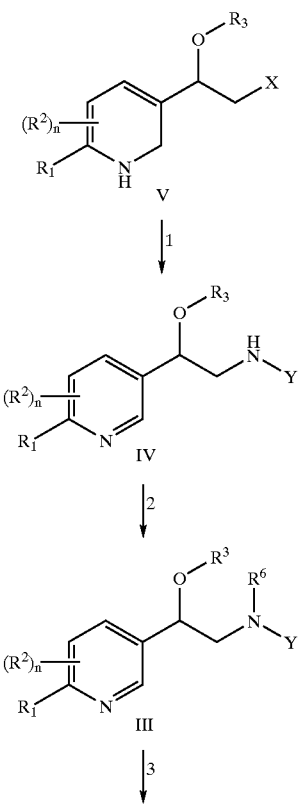

V

↓1

IV

↓2

III

↓3

-continued

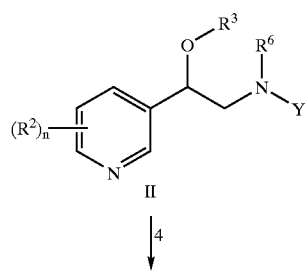

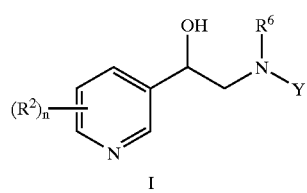

Scheme 2

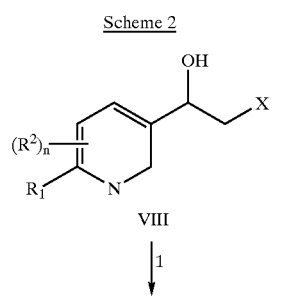

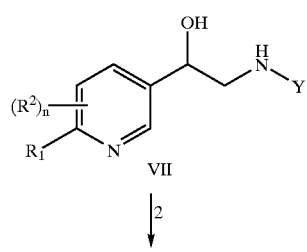

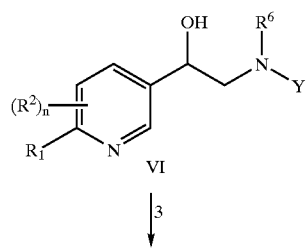

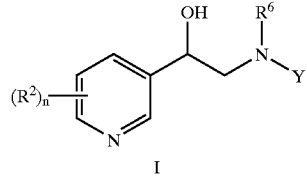

Scheme 3

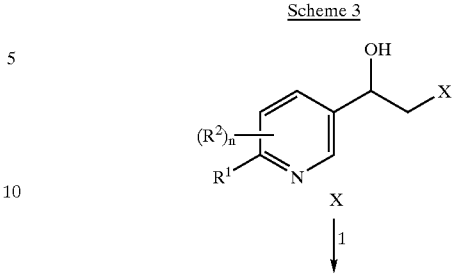

In reaction 1 of Preparation A, the 5-cyanopyridine compound of formula XIV is converted to the corresponding 5-formylpyridine compound of formula XIII by reacting XIV with a reducing agent, such as diisobutylaluminum hydride, in the presence of an aprotic solvent, such as toluene. The reaction is stirred at a temperature range between about 0° C. to about 10° C., preferably about 5° C., for a time period between about 15 minutes to about 45 minutes, preferably about 30 minutes. The resultant intermediate is then hydrolized with an acid or base, preferably methanol and sulfuric acid. The reaction mixture so formed is warmed to room temperature and stirred for an additional time period between about 30 minutes to about 90 minutes, preferably about 1 hour.

In reaction 2 of Preparation A, the 5-formylpyridine compound of formula XIII is converted to the corresponding 5-vinylpyridine compound of formula XII by reacting XIII with a methylating reagent, preferably prepared from methyltriphenylphosphonium bromide and potassium tert-butoxide, in the presence of a polar aprotic solvent, such as tetrahydrofuran. The resulting reaction mixture is stirred for a time period between about 15 minutes to about 45 minutes, preferably about 30 minutes, at a temperature range between about −40° C. to about 50° C., preferably about 5° C.

In reaction 3 of Preparation A, the 5-vinylpyridine compound of formula XII is converted to the corresponding diol compound of formula XI by reacting XII with a dihydroxylating agent, such as osmium tetroxide or potassium permanganate, preferably osmium tetroxide, with or without a co-oxidant, such as potassium ferricyanide, hydrogen peroxide, t-butyl hydroperoxide or N-methylmorpholine-N-oxide, preferably potassium ferricyanide, in the presence of tert-butanol and water. Such oxidations can be performed in the presence of a coordinating ligand, such as hydroquinidine 1,4-phthalazinediyl diether or hydroquinine 1,4-phthalazinediyl diether, which affords the enantiomerically enriched diol. The reaction mixture is stirred at a temperature range between about −30° C. to about 10° C., preferably about 5° C., for a time period between about 4 hours to about 18 hours, preferably about 6 hours.

In reaction 4 of Preparation A, the diol compound of formula XI is converted to the corresponding compound of formula X by reacting XI with the appropriate sulfonylchloride, such as p-toluenesulfonyl chloride, methanesulfonyl chloride, m-nitrobenzenesulfonyl chloride, p-nitrobenzenesulfonyl chloride or benzenesulfonyl chloride, preferably p-toluenesulfonyl chloride, in the presence of a base. Suitable bases which may be used include lower trialkylamines, pyridine, and pyridine derivatives. Preferred bases include, but are not limited to, triethylamine, diisopropylethylamine, pyridine, 2,4,6-collidine and 2,6-lutidine. Pyridine is the most preferred base. It is preferred that the solvent is a polar solvent such as (a) an ether derivative, including but not limited to, tetrahydrofuran, dioxane and dimethoxyethane; (b) chlorinated hydrocarbons, including but not limited to, carbon tetrachloride, chloroform and methylene chloride; (c) aromatic hydrocarbons including but not limited to benzene, toluene and xylene; (d) dimethylformamide; (e) N-methyl-2-pyrrolidinone; (f) dimethylacetamide; or (g) pyridine or any mixture of these solvents. Generally the most preferred solvent is pyridine. The reaction mixture is stirred at a temperature range between about 0° C. to about 10° C., preferably about 5° C., for a time period between about 6 hours to about 24 hours, preferably about 12 hours. To prepare compounds of formula X, wherein X is halo, the compound of formula XI, wherein X is tosylate, is reacted with a halogenating agent in a reaction inert solvent. The reaction is carried out at a temperature between 25° C. to the reflux temperature of the solvent utilized, preferably the reflux temperature of the solvent. Halogenating agents are compounds which are capable of transferring an organic substrate having a leaving group, i.e. sylate, which can be displaced by the halide ion. Preferred halogenating agents are lithium halides, such as lithium chlorides and the preferred solvent is a polar protic solvent, such as ethanol.

In reaction 5 of Preparation A, the compound of formula X is converted to the corresponding compound of formula IX by reacting X with a silyating agent, which include but are not limited to trialkylchlorosilanes, such as tert-butyldimethylsilyl chloride, triethylchlorosilane and triisopropylchlorosilane or alkylarylchlorosilanes, such as diphenylmethylchlorosilane, in the presence of a base and a polar protic solvent. A preferred silyating agent is tert-butyldimethylsilyl chloride. Suitable bases include, but are not limited to, triethylamine, N,N-diisopropylethylamine, imidazole, pyridine, 2,6-lutidine and N-methylmorpholine, preferably imidazole. Suitable polar protic solvents include, but are not limited to, dimethylacetamide, tetrahydrofuran, dimethylformamide, methylene chloride and chloroform, preferably dimethylformamide. The reaction is carried out at a temperature between about 0° C. to about 10° C., preferably about 5° C., and then warmed to room temperature over a time period between 14 hours to about 22 hours, preferably about 18 hours.

In reaction 1 of Scheme 1, the compound of formula V is converted to the corresponding compound of formula IV by reacting V with an amine of the formula, $H_2NY$, in the presence of N, N-diisopropylethylamine and a polar aprotic solvent, such as dimethyl sulfoxide. The reaction is stirred a temperature between 70° C. to about 90° C., preferably about 80° C., for a time period between about 5 hours to about 9 hours, preferably about 7 hours.

In reaction 2 of Scheme 1, the compound of formula IV is converted to the corresponding compound of formula III by reacting IV, wherein $R^6$ is an amine protecting group, with an organic acid anhydride, a dicarbonate, such as di-tert-butyl dicarbonate or an organic acid chloride. The term "amine protecting group" includes an organic radical which is readily attached to an amine nitrogen atom and which block said nitrogen atom from reacting with reagents and substrates used in and intermediates and transition state molecules formed in subsequent chemical transformations. The resulting reaction mixture is allowed to stir, at room temperature for a time period between about 2 hours to about 6 hours, preferably about 4 hours.

In reaction 3 of Scheme 1, the compound of formula III, wherein $R^1$ is halo, is converted to the corresponding compound of formula II by treating III with ammonium formate in the presence of palladium-on-carbon and a polar protic solvent, such as methanol. The reaction is allowed to stir at room temperature for a time period between about 1 hour to about 3 hours, preferably about 2 hours.

In reaction 4 of Scheme 1, the compound of formula II is converted to the corresponding compound of formula I by treating II with tetra-n-butylammonium fluoride in the presence of an aprotic solvent, such as tetrahydrofuran. The reaction is stirred at room temperature for a time period between about 3 hours to about 12 hours, preferably about 8 hours.

In reaction 1 of Scheme 2, the compound of formula VIII is converted to the corresponding compound of formula VII according to a procedure analogous to the procedure described above in reaction 1 of Scheme 1.

In reaction 2 of Scheme 2, the compound of formula VII is converted to the corresponding compound of formula VI according to a procedure analogous to the procedure described above in reaction 2 of Scheme 1.

In reaction 3 of Scheme 2, the compound of formula VI, wherein $R^1$ is halo, is converted to the corresponding compound of formula I according to a procedure analogous to the procedure described above in reaction 3 of Scheme 1.

In reaction 1 of Scheme 3, the compound of formula X is converted to the corresponding compound of formula IX by reacting X with a non-nucleophilic base, such as sodium hydroxide, potassium hydroxide, sodium hydride, potassium tert-butoxide or 1,8-diazabicyclo[5.4.0]undec-7-ene. The reaction is stirred, in a reaction inert solvent, at a temperature between about –20° C. to about 100° C. The preferred reaction inert solvent is a polar non-hydroxylic solvent such as an ether derivative including but not limited to tetrahydrofuran, dioxane and dimethoxyethane; chlorinated hydrocarbons including but not limited to carbon tetrachloride, chloroform and methylene chloride; aromatic hydrocarbons including but not limited to benzene, toluene and xylene; dimethylformamide; dimethylsulfoxide or any mixture of these solvents. Generally the most preferred solvent is tetrahydrofuran.

EXAMPLE 1

2-Chloro-5-formylpyridine

To a cooled 5° C., stirred solution of 2-chloro-5-cyanopyridine (25.0 grams) in anhydrous toluene (540 mL) was added a 1M solution of diisobutylaluminum hydride (189 mL) over a 30 minute period. The resulting red-colored solution was treated with methanol (50 mL) and 2M sulfuric acid (150 mL), sequentially. The resulting biphasic solution was allowed to warm to ambient temperature and stirred for 1 hour. The reaction mixture was extracted with ethyl acetate, the combined organic layers were washed with saturated aqueous sodium bicarbonate and saturated aqueous brine. The organic phase was stirred over activated charcoal for 20 minutes, dried over anhydrous sulfate and concentrated in vacuo to afford the title compound as a light-yellow colored solid, 23.5 grams $^1$H NMR (400 MHz, $CDCl_3$) δ=10.08 (s, 1H); 8.85 (s, 1H); 8.12 (d, 1H); 7.50 (d, 1H).

EXAMPLE 2

2-Chloro-5-vinylpyridine

To a cooled 5° C., stirred slurry of methyltriphenylphosphonium bromide (75.7 grams) in tetrahydrofuran (530 mL)

was added potassium t-butoxide (23.8 grams) portionwise over a 5 minute period to produce a yellow slurry. After 30 minutes, 2-chloro-5-formylpyridine (25.0 grams) was added in one portion to produce a purple colored slurry. After an additional 30 minutes, the reaction mixture was treated with saturated aqueous ammonium chloride (200 mL) and a majority of the tetrahydrofuran was removed in vacuo. The resulting mixture was washed with ethyl acetate, the combined organic layers washed with saturated aqueous brine, stirred over activated charcoal for 20 minutes, dried over anhydrous sodium sulfate and concentrated in vacuo. The resulting semi-solid was stirred for 30 minutes with a solution of 2:1 diethyl ether/petroleum ether (375 mL), filtered and the solids washed with an additional portion of 2:1 diethyl ether/petroleum ether (300 mL). The combined filtrates were concentrated in vacuo, pre-loaded on 60 grams of silica gel and chromatographed over 700 grams of silica gel eluting with a gradient of ethyl acetate(0–8%)/hexanes to afford the title compound as a colorless oil, 15.2 grams $^1$H NMR (400 MHz, CDCl$_3$): δ=8.35 (s, 1H); 7.69 (d,1H); 6.65 (dd, 1H); 5.79 (d, 1H); 5.40 (d, 1H).

EXAMPLE 3

(R)-1-(6-Choro-pyridin-3-yl)-ethane-1,2-diol

To a cooled 5° C., stirred slurry of AD__Mix-β® (150 g) in water (530 mL) and t-butanol (450 mL) was added a solution of 2-chloro-5-vinylpyridine (15.0 grams) in t-butanol (80 mL). After 6 hours, solid sodium sulfite (160 grams) was added and the resulting slurry was allowed to stir at ambient temperature for 30 minutes. This mixture was extracted with ethyl acetate (3 times), the combined organic layers were washed with saturated aqueous brine, dried over sodium sulfate and concentrated in vacuo. The resulting oil was chromatographed on 500 grams of silica gel eluting with a gradient of ethyl acetate (70–80%)/hexanes to afford the title compound as a colorless oil, 17.8 grams $^1$H NMR (400 MHz, CDCl$_3$): δ=8.35 (s, 1H); 7.71 (d, 1H); 7.30 (d, 1H); 4.85 (dd, 1H); 3.63 (dd, 1H).

EXAMPLE 4

(R)-Toluene-4-sulfonic acid 2-(6-chloro-pyridin-3-yl)-2-hydroxy-ethyl ester

To a cooled 5° C., stirred solution of (R)-1-(6-chloro-pyridin-3-yl)-ethane-1,2-diol (17.8 grams) in anhydrous pyridine (100 mL) was added p-toluenesulfonyl chloride (19.5 grams) in one portion. After 20 minutes, the cooling bath was removed and stirring was continued an additional 12 hours. The reaction solution was concentrated in vacuo, azeotroped with toluene (2 times), diluted ethyl acetate, washed with half-saturated aqueous brine, saturated aqueous brine, dried over sodium sulfate and concentrated in vacuo. The resulting solids were recrystallized from ethyl acetate/hexanes to afford the title compound as colorless crystals, 23.3 grams $^1$H NMR (400 MHz, CDCl$_3$)=8.29 (s, 1H); 7.72 (d, 2H); 7.64 (d, 1H); 7.32 (d, 2H); 7.28 (d, 1H); 5.00 (dd, 1H); 4.09 (AB pattern, 2H); 2.44 (s, 3H).

EXAMPLE 5

(R)-Toluene-4-sulfonic acid 2-(tert-butyl-dimethyl-silanyloxy)-2-(6-chloro-pyridin-3-yl)-ethel ester To a cooled 5° C., stirred solution of (R)-toluene-4-sulfonic acid 2-(6-chloro-pyridin-3-yl)-2-hydroxy-ethyl ester (4.9 grams) and imidazole (2.0 grams) in anhydrous dimethyformamide (14 mL) was added t-butyldimethylsilyl chloride (2.8 grams). The mixture was allowed to warm to room temperature and stirring was continued for 18 hours. Ethyl acetate was added, followed by washing with water (2 times), drying over sodium sulfate and concentrating in vacuo to afford an oil. Chromatography (Flash 40M®) utilizing 10% ethyl acetate/hexanes afforded the title compound as a colorless oil, 5.6 grams $^1$H NMR (400 MHz, CDCl$_3$): δ=8.24 (s, 1H); 7.64 (d, 2H); 7.56 (d, 1H); 7.28 (d, 2H); 7.23 (d,1H); 4.88 (dd, 1H); 3.95 (AB pattern, 2H); 2.44 (s, 3H); 0.83 (s, 6H); 0.06 (s, 3H); −0.07 (s, 3H).

EXAMPLE 6

[2r-(tert-Butyl-dimethylsilanyloxy)-2-(6-chloro-pyridin-3-yl)-ethyl]-[2-(4-nitrophenyl-ethyl]-carbamic acid tert-butyl ester A solution of (R)-toulene-4-sulfonic acid 2-(tert-butyl-dimethyl-silanyloxy)-2-(6-chloro-pyridin-3-yl)-etyl ester (2.2 grams), 4-nitrophenethylamine (1.6 grams) and N,N-diisopropylethylamine (0.8 grams) in DMSO were heated at 80° C. for 7 hours. After cooling, di-t-butyl dicarbonate (2.1 grams) was added and the resulting solution was stirred at ambient temperature for 4 hours. Ethyl acetate was added, followed by washing with water (2 times), drying over sodium sulfate and concentrating in vacuo to afford oil. Chromatography (Flash 12S®) utilizing 5–10% ethyl acetate/hexanes afforded the title compound as a colorless oil, 1.2.

EXAMPLE 7

[2R-(4-Aminophenyl)-ethyl]-[2-(tert-butyl-dimethylsilanyloxy)-2-pyridin-3-yl-ethyl]-carbamic acid tert-butyl ester To a stirred solution of [2-(tert-butyl-dimethylsilanyloxy)-2-(6-chloro-pyridin-3-yl)-ethyl]-[2-(4-nitrophenyl)-ethyl]-carbamic acid tert-butyl ester (0.6 grams) and ammonium formate (1.4 grams) in methanol (10 mL) was added 10% palladium-on-carbon (0.6 grams). After 2 hours, the mixture was filtered through Celite®, the filtrate concentrated in vacuo and the residue partitioned between ethyl acetate and water. The organic phase was washed with brine, dried over sodium sulfate and concentrated in vacuo to afford the title compound as a yellow oil, 0.5 grams.

What is claimed is:
1. A process for preparing a compound of the formula

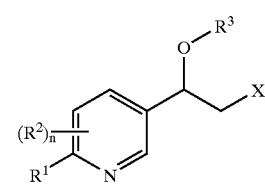

IX wherein n is 0, 1, 2 or 3;

R$^1$ is hydrogen or halo;

each R$^2$ is independently hydrogen, halo, trifluoromethyl, cyano, SR$^4$, OR$^4$, SO$_2$R$^4$, OCOR$^5$, or (C$_1$–C$_{10}$)alkyl wherein the alkyl group is optionally substituted by hydroxy, halo, cyano, N(R$^4$)$_2$, SR$^4$, trifluoromethyl, OR$^4$, (C$_3$–C$_8$)cycloalkyl, (C$_6$–C$_{10}$)aryl, NR$^4$COR$^5$, COR$^5$, SO$_2$R$^5$, OCOR$^5$, NR$^4$SO$_2$R$^5$ and NR$^4$CO$_2$ R$^4$;

R$^3$ is tetrahydrofuranyl, tetrahydropyranyl or a silyl protecting group;

X is halo, methanesulfonyloxy, benzenesulfonyloxy, p-toluenesulfonyloxy, m-nitrobenzenesulfonyloxy or p-nitrobenzenesulfonyloxy;

R$^4$ and R$^5$, for each occurrence, are each independently selected from hydrogen, (C$_1$–C$_{10}$)alkyl, (C$_1$–C$_{10}$)

alkoxy, $(C_3-C_8)$cycloalkyl,$(C_6-C_{10})$aryl, $(C_2-C_9)$ heterocycloalkyl, $(C_2-C_9)$heteroaryl or $(C_1-C_6)$aryl wherein the alkyl group is optionally substituted by the group consisting of hydroxy, halo, carboxy, $(C_1-C_{10})$ alkyl-$CO_2$, $(C_1-C_{10})$alkylsulfonyl, $(C_3-C_8)$cycloalkyl, $(C_1-C_{10})$alkoxy, or $(C_1-C_6)$alkyl; and wherein the aryl, heterocycloalkyl and heteroaryl groups are optionally substituted by one to four groups consisting of halo, nitro, oxo, $((C_1-C_6)$alkyl$)_2$amino, pyrrolidine, piperidine, $(C_1-C_{10})$alkyl, $(C_1-C_{10})$ alkoxy, $(C_1-C_{10})$alkylthio and $(C_1-C_{10})$alkyl wherein the alkyl group is optionally substituted by one to four groups selected from hydroxy, halo, carboxy, $(C_1-C_6)$ alkyl-$CO_2$, $(C_1-C_6)$alkylsulfonyl, $(C_3-C_8)$cycloalkyl and $(C_1-C_6)$alkoxy;

or $R^5$ is $N(R^4)_2$ wherein $R^4$ is as defined above; comprising reacting a compound of the formula

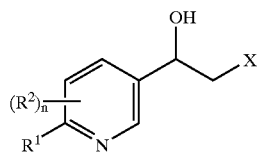

X wherein n, $R^1$, $R^2$ and X are as defined above, with a silyating agent in the presence of a base.

2. A process according to claim 1, wherein the silyating agent is tert butyldimethylsilyl chloride, triethylchlorosilane, triisopropylchlorosilane or diphenylmethylchlorosilane.

3. A process according to claim 1, wherein the base is triethylamine, N,N-diisopropylethylamine, imidazole, pyridine, 2,6-lutidine or N-methylmorpholine.

4. A process according to claim 1, wherein the compound of the formula

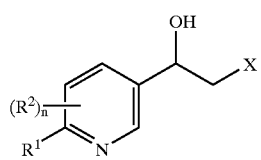

X is formed by reacting a compound of the formula

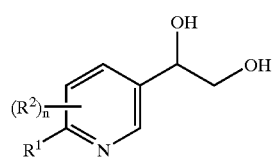

XI wherein n, $R^1$ and $R^2$ are as defined above, with a sulfonyl chloride in the presence of a base, and in the case wherein X is halo, by further treatment with a metal halide.

5. A process according to claim 4, wherein the sulfonyl chloride is p-toluenesulfonyl chloride, methanesulfonyl chloride, m-nitrobenzenesulfonyl chloride, p-nitrobenzenesulfonyl chloride or benezenesulfonyl chloride.

6. A process according to claim 4, wherein the base is triethylamine, diisopropylethylamine, pyridine, 2,4,6-collidine or 2,6-lutidine.

7. A process according to claim 4, wherein the metal halide is lithium chloride.

8. A process according to claim 4, wherein the compound of the formula

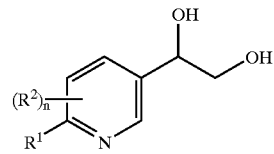

XI is formed by reacting a compound of the formula

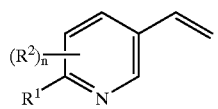

XII wherein n, $R^1$ and $R^2$ are as defined above, with a dihydroxylating agent, with or without a co-oxidant and/or a coordinating ligand.

9. A process according to claim 8, wherein the dihydroxylating agent is osmium tetroxide or potassium permanganate.

10. A process according to claim 8, wherein the co-oxidant is potassium ferricyanide, hydrogen peroxide, tert-butyl hydroperoxide or N-methylmorpholine-N-oxide.

11. A process according to claim 8, wherein the coordinating ligand is hydroquinidine 1,4-phthalazinediyl diether or hydroquinine 1,4-phthalazinediyl diether.

12. A process according to claim 8, wherein the compound of the formula

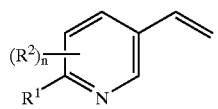

XII is formed by reacting a compound of formula V

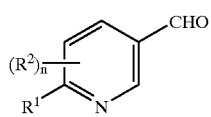

XIII wherein n, $R^1$ and $R^2$ are as defined above, with a methylating reagent.

13. A process according to claim 12, wherein the methylating reagant is prepared from methyltriphenylphosphonium bromide and potassium tert-butoxide.

14. A process according to claim 12, wherein the compound of the formula

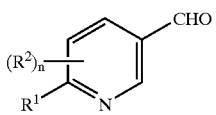

XIII is formed by reducing a compound of the formula

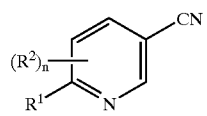

XIV wherein n, $R^1$ and $R^2$ are as defined above, with a reducing agent followed by hydrolysis with an acid or base.

15. A process according to claim 14, wherein the reducing agent is diisobutylaluminum hydride.

16. A process according to claim 14, wherein the acid is sulfuric acid.

17. A process for preparing a compound of the formula

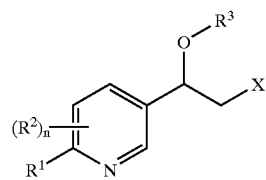

IX wherein n is 0, 1, 2 or 3;

$R^1$ is hydrogen or halo;

each $R^2$ is independently hydrogen, halo, trifluoromethyl, cyano, $SR^4$, $OR^4$, $SO_2R^4$, $OCOR^5$, or $(C_1–C_{10})$alkyl wherein the alkyl group is optionally substituted by hydroxy, halo, cyano, $N(R^4)_2$, $SR^4$, trifluoromethyl, $OR^4$, $(C_3–C_8)$cycloalkyl, $(C_6–C_{10})$aryl, $NR^4COR^5$, $COR^5$, $SO_2R^5$, $OCOR^5$, $NR^4SO_2R^5$ and $NR^4CO_2\,R^4$;

$R^3$ is tetrahydrofuranyl, tetrahydropyranyl or a silyl protetcting group;

X is halo, methanesulfonyloxy, benzenesulfonyloxy, p-toluenesulfonyloxy, m-nitrobenzenesulfonyloxy or p-nitrobenzenesulfonyloxy;

$R^4$ and $R^5$, for each occurrence, are each independently selected from hydrogen, $(C_1–C_{10})$alkyl, $(C_1–C_{10})$alkoxy, $(C_3–C_8)$cycloalkyl, $(C_6–C_{10})$aryl, $(C_2–C_9)$heterocycloalkyl, $(C_2–C_9)$heteroaryl or $(C_1–C_6)$aryl wherein the alkyl group is optionally substituted by the group consisting of hydroxy, halo, carboxy, $(C_1–C_{10})$alkyl-$CO_2$, $(C_1–C_{10})$alkylsulfonyl, $(C_3–C_8)$cycloalkyl, $(C_1–C_{10})$alkoxy, or $(C_1–C_6)$alkyl; and wherein the aryl, heterocycloalkyl and heteroaryl groups are optionally substituted by one to four groups consisting of halo, nitro, oxo, $((C_1–C_6)$alkyl$)_2$amino, pyrrolidine, piperidine, $(C_1–C_{10})$alkyl, $(C_1–C_{10})$alkoxy, $(C_1–C_{10})$alkylthio and $(C_1–C_{10})$alkyl wherein the alkyl group is optionally substituted by one to four groups selected from hydroxy, halo, carboxy, $(C_1–C_6)$alkyl-$CO_2$, $(C_1–C_6)$alkylsulfonyl, $(C_3–C_8)$cycloalkyl and $(C_1–C_6)$alkoxy;

or $R^5$ is $N(R^4)_2$ wherein $R^4$ is as defined above;

comprising
(a) reacting a compound of the formula

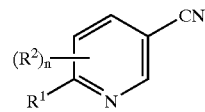

XIV wherein n, $R^1$ and $R^2$ as defined above, with a reducing agent followed by hydrolsis with an acid or base;
(b) reacting the intermediate of formula XIII so formed

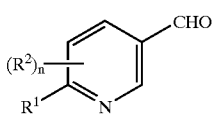

XIII wherein n, $R^1$ and $R^2$ are as defined above, with a methylating agent to form a vinylpyridine compound of the formula

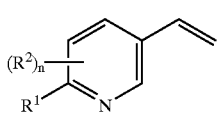

XII (c) reacting the vinylpyridine compound so formed in step (b) with a dihydroxylating agent, with or without a co-oxidant and/or a coordinating ligand to form the compound of the formula

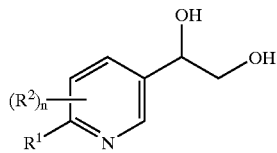

XI wherein n, $R^1$ and $R^2$ are as defined above;
(d) reacting the compound of formula XI so formed with a sulfonyl chloride in the presence of a base to form the compound of the formula X

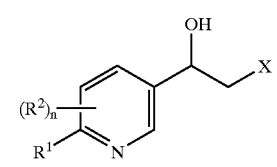

X wherein n, $R^1$, $R^2$ and X are as defined above; and
(e) reacting the compound of formula X so formed with silyating agent in the presence of a base.

* * * * *